(12) United States Patent
Lanier

(10) Patent No.: US 9,717,857 B2
(45) Date of Patent: Aug. 1, 2017

(54) MEDICAL INJECTION DEVICE

(71) Applicant: Becton Dickinson France, Le Pont de Claix (FR)

(72) Inventor: Romain Lanier, Veurey-Voroize (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 14/409,358

(22) PCT Filed: Jun. 26, 2013

(86) PCT No.: PCT/EP2013/063373
§ 371 (c)(1),
(2) Date: Dec. 18, 2014

(87) PCT Pub. No.: WO2014/001386
PCT Pub. Date: Jan. 3, 2014

(65) Prior Publication Data
US 2015/0196715 A1   Jul. 16, 2015

(30) Foreign Application Priority Data
Jun. 27, 2012 (EP) ..................................... 12305753

(51) Int. Cl.
*A61M 37/00* (2006.01)
*A61M 5/315* (2006.01)
*A61M 5/145* (2006.01)

(52) U.S. Cl.
CPC ...... *A61M 5/31513* (2013.01); *A61M 5/1452* (2013.01); *A61M 5/1458* (2013.01); *A61M 2005/14573* (2013.01)

(58) Field of Classification Search
CPC .. A61M 2005/2086; A61M 2005/2414; A61M 2005/31508; A61M 2005/3151; A61M 2005/31516; A61M 2005/3246
(Continued)

(56) References Cited

U.S. PATENT DOCUMENTS 6,193,695 B1   2/2001  Rippstein, Jr.
7,947,020 B2 *  5/2011  Thayer ................ A61M 5/3234
                                                        604/195

(Continued)

FOREIGN PATENT DOCUMENTS

EP   0925798 A2   6/1999
FR   1048267 A    12/1953
(Continued)

*Primary Examiner* — Phillip Gray
(74) *Attorney, Agent, or Firm* — The Webb Law Firm

(57) ABSTRACT

The invention relates to a medical injection device comprising a container body (1) and a stopper (2) in gliding engagement within the container body (1) for expelling a fluid (3) through an opening of said container body (1), wherein: —at least the distal portion (20) of the stopper (2) that is in contact with the fluid (3) is made of a thermoplastic polyolefin, —the stopper (2) further comprises at least one O-ring (4, 4') maintained in at least one peripheral groove (210, 210'), —said O-ring (4, 4') is made of a butyl-type rubber; and —the cross-section of said peripheral groove (210, 210') is designed so as to compress both axially and radially the O-ring (4) when said O-ring (4) is engaged in the peripheral groove (210) between the stopper (2) and the inner wall (10) of the container body (1).

26 Claims, 4 Drawing Sheets

(58) Field of Classification Search
USPC .................. 604/154, 218–231, 181, 187
See application file for complete search history.

(56) References Cited

U.S. PATENT DOCUMENTS

| | | | | |
|---|---|---|---|---|
| 8,226,610 | B2 * | 7/2012 | Edwards | A61M 5/19 206/363 |
| 8,277,422 | B2 * | 10/2012 | Oliver | A61M 5/3234 604/110 |
| 2009/0024095 | A1 | 1/2009 | Frezza | |
| 2009/0326458 | A1 | 12/2009 | Chong et al. | |

FOREIGN PATENT DOCUMENTS

| | | |
|---|---|---|
| JP | 201275784 A | 4/2012 |
| RU | 2373962 C1 | 11/2009 |
| WO | 2008116908 A1 | 10/2008 |
| WO | 2012049480 A1 | 4/2012 |

* cited by examiner

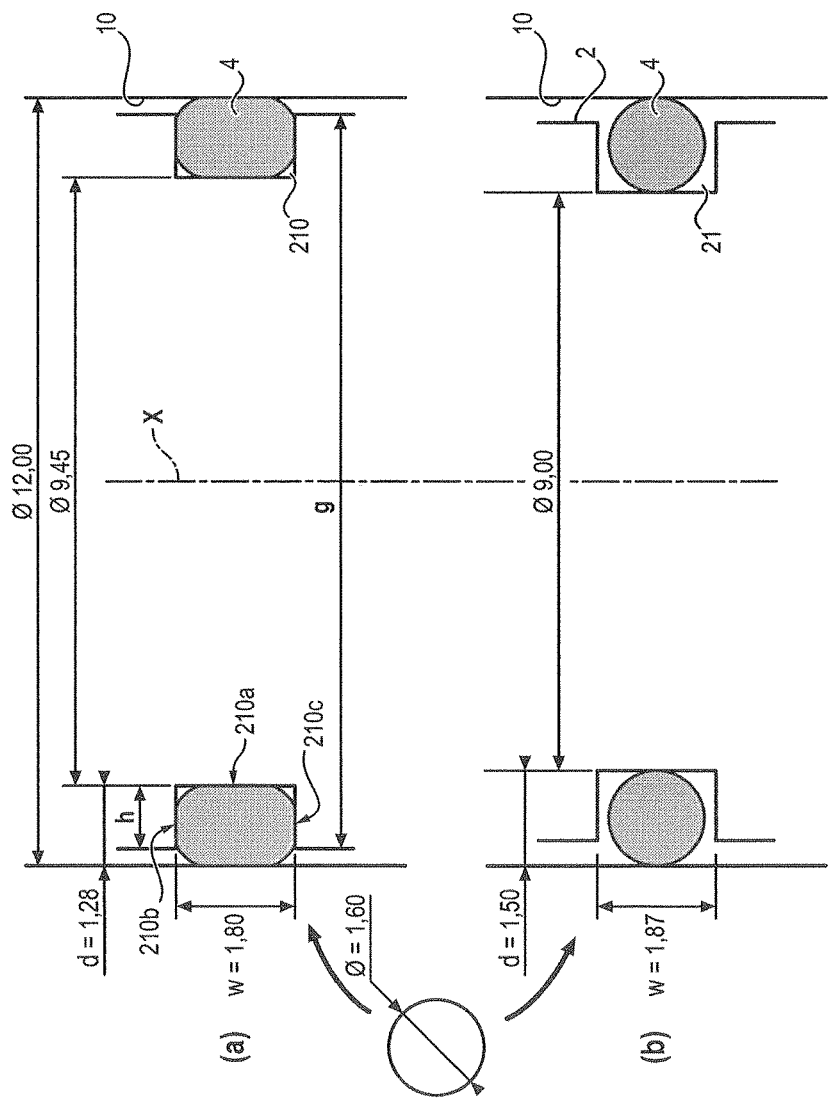

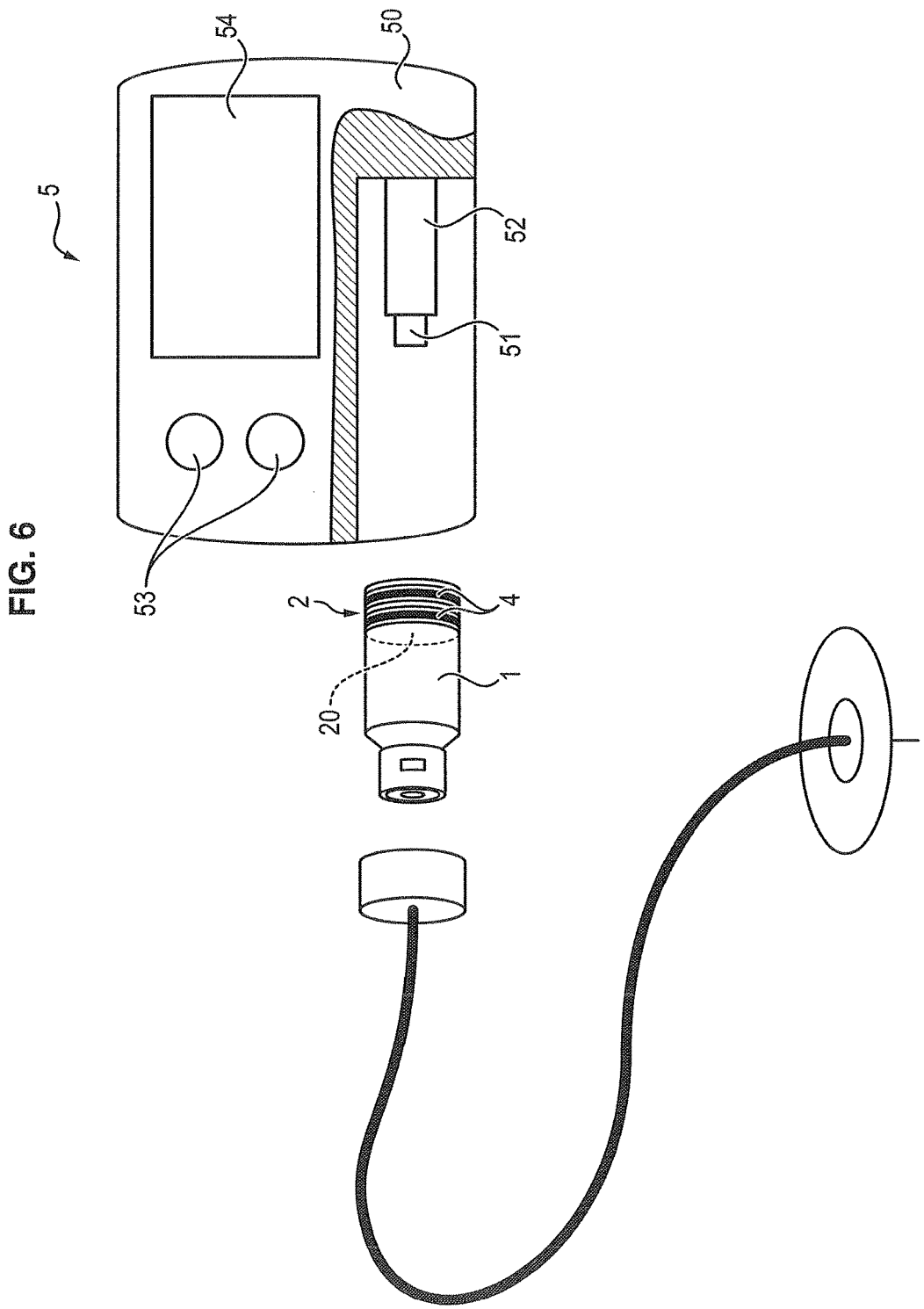

MEDICAL INJECTION DEVICE

CROSS REFERENCE TO RELATED APPLICATIONS

This application is the United States national phase of International Application No. PCT/EP2013/063373 filed Jun. 26, 2013, and claims priority to European Patent Application No. 12305753.1 filed Jun. 27, 2012, the disclosures of which are hereby incorporated in their entirety by reference.

FIELD OF THE INVENTION

The present invention relates to a medical injection device and to a pump including such a device.

BACKGROUND OF THE INVENTION

Medical containers that comprise a sealing stopper in a gliding engagement within a container body are widely used to deliver drug by injection to a patient.

Injection devices usually comprise such container which is intended to receive the drug to be injected and a plunger rod intended to move the stopper within the body of the container so as to expel the drug therefrom at the time of injection.

Either it is necessary to use an empty disposable injection device to withdraw the drug to be injected from a vial or to use disposable prefilled injection device.

Prefilled injection devices are often preferred because they are more convenient, safe and efficient and may reduce risk of cross contamination during preparation of the injection.

Many different types of injection devices, including syringes, cartridges and auto-injectors have been designed for administering drugs.

Infusion pumps are known to be used for delivering or dispensing drugs—such as insulin in case of diabetes—in a more comfortable way for the patient.

Such pumps comprise a pump housing adapted to receive an injection device containing the prescribed drug and an associated infusion set.

They usually include a small drive motor connected to a plunger rod for motor-driven advancement of the stopper present in the container in order to administer the drug to the patient.

Programmable control means can be provided for operating the drive motor continuously or at periodic intervals to obtain a closely controlled and accurate delivery of the drug over an extended period of time.

In this framework, the stopper typically has slow motion and is displaced on small distances in a given period of time.

As a consequence, it is necessary to ensure smooth gliding of the stopper within the container body to avoid any displacement by fits and starts.

In particular, the phenomenon known as "stick-slip effect" has to be avoided because it could lead to the delivery of an inaccurate dose of drug to the patient.

In order to improve gliding performance of the stopper, a lubricant coating may be applied onto the inner wall of the container body and/or onto the stopper.

Meanwhile, the stopper needs to provide a good sealing with respect to the container body in order to avoid leakage of drug from the container and to avoid any contamination of the drug from the outside of the container.

Traditional injections devices comprise a container made of glass or plastic and a stopper made of elastomeric material.

Due to the softness of the elastomer, the stopper itself is able to ensure the sealing with respect to the container body.

However, said softness may also be responsible for inaccurate dose delivery.

Indeed, when a pushing effort is applied to the stopper via the plunger rod, the stopper may first absorb the effort by its own compression, and may only begin gliding later on.

In such case, the dose delivered to the patient is different from the dose expected from the displacement of the plunger rod.

Moreover, in some cases, rubber and soft materials of the like may not be appropriate due to their incompatibility with the drug contained inside the container body of the injection device.

A more compatible material may thus be selected.

Therefore for the different above-mentioned reasons, it may be preferable to choose a rigid material for the stopper, e.g. polyethylene or the like.

Indeed, a stopper in this kind of material is not likely to deform under the pushing effort of the plunger rod and may thus allow improving the accuracy of the dose delivery.

In such case, it is necessary to provide at least a sealing ring around the stopper in order to ensure the sealing between the stopper and the container body, as such rigid materials usually lead to the leakage of the drug contained inside the container body.

The document US 2009/0326458 discloses a medical injection device that comprises a container and a rigid polyethylene stopper having at least one O-ring made of an elastomer, e.g. rubber or silicone, that is maintained in a groove of the stopper.

FIG. 1 illustrates a schematic sectional view of such stopper 2 having two peripheral grooves 21, 21' and two O-rings 4, 4' in order to be in gliding engagement within a container body 1, the inner wall 10 of the container body 1 being coated with a lubricant layer, e.g. a silicone-free lubricant.

However, this device can present several limitations.

First of all, the lubricant coating applied forms droplets that may be released in the drug 3.

Indeed, there is a strong concern about the presence of particles in the drugs, because they may alter the efficiency of the drug.

It is thus desired to limit the release of particles, in particular from the lubricant coating.

Further, due to their intrinsic properties, the silicone O-rings present certain permeability to moisture and air and do not provide either an efficient sealing of the injection device or a good drug isolation.

In addition, it is known that a back-and-forth movement of the stopper occurs under pump rod displacement, which can often be detrimental to the reactivity of the injection device and the accuracy of the dose delivered to the patient.

BRIEF DESCRIPTION OF THE INVENTION

An object of the invention is thus to provide a medical injection device that overcomes the drawbacks of the known devices.

Such an improved medical injection device also leads to a more accurate dose of drug delivered to the patient, especially when using an infusion pump.

In particular, the medical injection device of the invention allows a more efficient gliding of the stopper within the container body while providing an improved sealing, thus avoiding drug leakage and drug contamination.

Finally, the materials of the medical injection device of the invention are compatible with the drug contained into the device and do not alter the properties of the drug, even over a long period of time.

One embodiment of the invention is a medical injection device comprising a container body and a stopper in gliding engagement within the container body for expelling a fluid through an opening of said container body, wherein:
  at least the distal portion of the stopper that is in contact with the fluid is made of a thermoplastic polyolefin,
  the stopper further comprises at least one O-ring maintained in at least one peripheral groove.
Said medical injection device is characterized in that:
  said at least one O-ring is made of a butyl-type rubber; and
  the cross-section of said at least one peripheral groove of the stopper is designed so as to compress both axially and radially the at least one O-ring when said at least one O-ring is engaged in the peripheral groove between the stopper and the inner wall of the container body.

In this application, the distal end of a component or of a device must be understood as meaning the end furthest from the hand of the user and the proximal end must be understood as meaning the end closest to the hand of the user. In particular, in the present application, the container being for example intended to be used as a prefilled cartridge for an infusion pump, the distal end must be understood as meaning the end closest to the top of the container (i.e. the end of the container provided with the opening to be sealed with a septum) and the proximal end must be understood as being the end closest to the bottom of the container.

The cross-section of an element must be understood as meaning the shape of said element exposed by making a straight cut of this element according to a plane passing through the longitudinal axis of the container body. When the element has a circular cross-section, the diameter of said element is defined as being the diameter of said circle.

In accordance with an embodiment of the invention, the axial compression of said at least one O-ring is advantageously at least 14.4% and the radial compression is preferably at least 20%.

The diameter of said at least one O-ring at rest is greater than the width of the respective at least one peripheral groove of the stopper.

In a preferred embodiment, the material of said at least one O-ring is bromobutyl.

The stopper may preferably comprise at least two O-rings maintained in two corresponding peripheral grooves of the stopper.

In such case, the distance between said two O-rings is preferably at least equal to the diameter of the stopper.

Said O-rings may have a circular cross-section with different diameters.

In such case, the diameter of the distal O-ring is preferably larger than the diameter of the proximal O-ring.

Advantageously, the at least one peripheral groove has a U-shaped cross-section comprising a side wall extending axially and two parallel lateral walls extending radially from the side wall, said at least one peripheral groove forming with the container body an O-ring housing having a rectangular cross-section for said at least one O-ring.

Preferably, the depth of said O-ring housing is smaller than the width thereof.

According to an embodiment, the diameter of said at least one O-ring is of 1.60 mm and said at least one peripheral groove has a U-shaped cross-section defined by a width smaller than or equal to 1.85 mm and a height greater than or equal to 0.86 mm. Preferably, said at least one peripheral groove has a U-shaped cross-section defined by a width comprised between 1.60 mm and 1.80 mm and a height greater than or equal to 0.95 mm.

According to an embodiment of the invention, the device consists of a prefillable injection device.

For example, said device may be prefilled with insulin.

According to an embodiment of the invention, said at least one O-ring and/or at least part of the inner wall of the container body is coated with a lubricant layer.

Said lubricant layer may advantageously be a gel comprising a mixture of acrylate-based silicone, vinyl-based silicone and polydimethylsiloxane.

Another embodiment of the invention is a pump for delivering a fluid to a patient, comprising:
  a housing for receiving an injection device as described above, containing said fluid,
  a plunger rod arranged in said housing to be connected to the proximal part of the stopper of said injection device, and
  a motor for driving said plunger rod so as to expel the fluid from a distal opening of the injection device.

BRIEF DESCRIPTION OF THE DRAWINGS

Further features and advantages of the invention will become apparent from the detailed description to follow, with reference to the appended drawings, in which:

FIG. 5 is a schematic sectional view of a stopper according to an embodiment of the invention (5a) and of a stopper of a known injection device (5b), for a given O-ring;

FIG. 6 is a schematic view of a pump including an injection device according to an embodiment of the invention.

DETAILED DESCRIPTION OF EMBODIMENTS OF THE INVENTION

Figure 3:
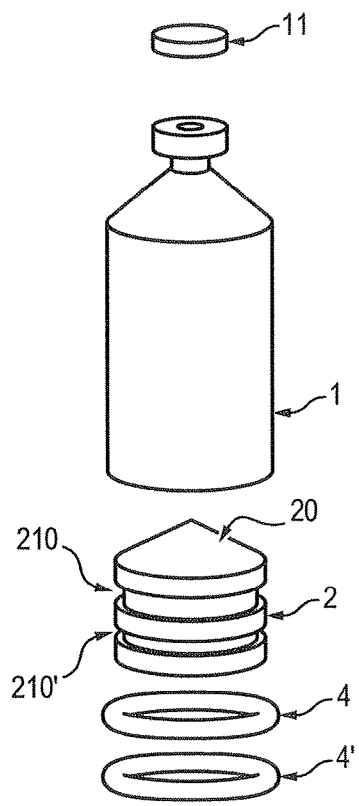
FIG. 3 is an exploded view of a medical injection device according to an embodiment of the invention.

FIG. 3 illustrates a medical injection device according to an embodiment of the invention.

The container body 1 may be in glass or in plastic, especially in cyclic polyolefin.

The container body 1 is sealed by a septum 11.

Figure 2:
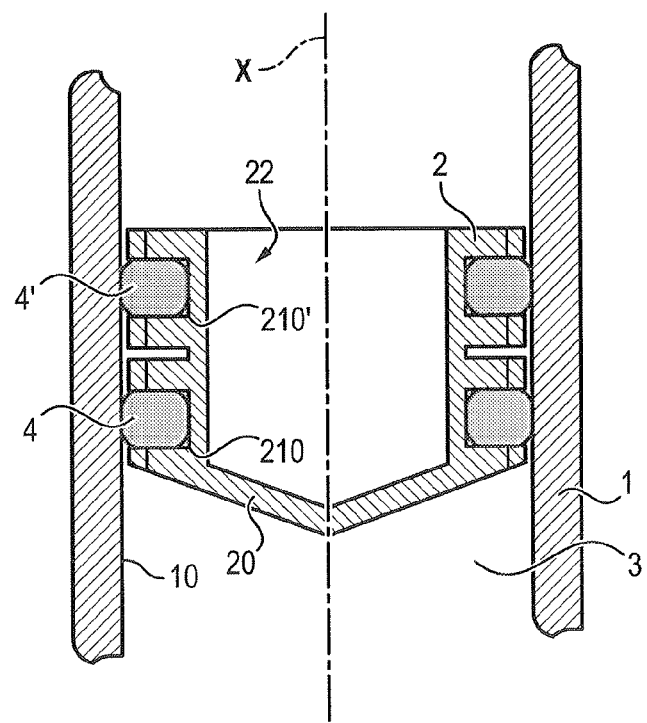
FIG. 2 is a schematic sectional view of the gliding engagement of a stopper within a container body, according to an embodiment of the invention.

The stopper 2 is in gliding engagement within the container body 1 along an axial direction X, as shown in FIG. 2.

As can be seen on FIG. 2, the stopper 2 has the general form of a cylindrical shell with a central opening that is designed so as to cooperate with a plunger rod (not shown) in view of the activation of the stopper for the dose delivery of a drug.

The cooperation between the plunger rod and the stopper 2 may be obtained by any suitable means, such as gluing, threading, snapping, etc.

The stopper 2 has a distal portion 20 that is intended to be in contact with the pharmaceutical drug contained inside the container body 1 and that faces the distal opening of the container body 1 through which the solution has to be expelled.

In the illustrated embodiment, the distal portion 20 has a conical shape but it can be flat or could have any other suitable shape.

The stopper 2 may be made of a single material or of mixture of several materials (e.g. plastics and elastomer).

Preferably, the stopper 2 has a rigid part that is made of a rigid material, especially in a thermoplastic polyolefin to provide some rigidity to the stopper 2 in order to increase the accuracy of the drug delivery.

Indeed, contrary to rubber stoppers, the stopper 2 made of such rigid material is not deformed when the plunger rod is activated.

According to a preferred embodiment of the invention, at least the distal portion 20 of the stopper 2 that is in contact with the pharmaceutical drug is made of a cyclic polyolefin.

Such a material is also advantageous because it is compatible with drugs such as, for example, insulin, even over a long period of time, since it does not release elements into the drug.

The stopper 2 can also be made of polypropylene but in this case it would be preferable to have a protective coating applied on its surface in order to avoid extraction of elements from the stopper 2 into the drug to be injected.

Moreover, in order to ensure the right sealing of the stopper 2 with regard to the container body 1, at least one O-ring 4 or 4' is provided at the interface between the stopper 2 and the container body 1.

Such an O-ring has a ring shape with a circular cross-section.

As compared to other shapes of sealing rings, an O-ring has the advantage of being easier to mount on the stopper.

In addition, an O-ring also has the advantage of providing a progressive contact with the inner wall of the barrel, which in turns provides a progressive contact pressure profile which is favorable to a good gliding.

More precisely, the O-ring 4 or 4' is positioned on the stopper 2 before the stopper 2 is placed inside the container body 1.

To that end, at least one peripheral groove 210 or 210' is provided in the peripheral wall of the stopper 2.

Said peripheral groove 210 or 210' is dimensioned and positioned in order to maintain an O-ring 4 or 4' and avoid any leakage of the contents of the container body 1 during storage but also when the stopper 2 is in motion.

As shown on FIGS. 2 and 3, at least two O-rings 4, 4' are provided at the interface between the stopper 2 and the container body 1, that is, in the peripheral grooves 210 and 210'.

A pair of O-rings 4, 4' is preferred as it enables a greater stability of the stopper 2, and therefore constitutes a preferred embodiment of the invention.

Each of said O-rings 4, 4' is maintained in a respective peripheral groove 210, 210' of the stopper 2 due to the specific geometry of the cavity formed by the peripheral groove 210, 210'.

In a preferred embodiment of the invention, the O-rings 4 and 4' are identical as well as the corresponding peripheral grooves 201 201', but in another embodiment, the O-rings can have circular cross-sections with different diameters and then, the geometry of the cavity forming the peripheral groove is adapted in order to correctly receive the corresponding O-ring.

Preferably, the distance between the two O-rings 4, 4' is at least equal to the diameter of the stopper 2 in order to prevent any rotation of the stopper 2 with respect to an O-ring 4 or 4'.

According to a preferred embodiment of the invention, the O-ring 4 or 4' is made of butyl-type rubber. For example, the O-ring 4 or 4' is made of bromobutyl, such as, for instance, a bromobutyl rubber sold by Exxon™ under the name Bromobutyl Rubber Grade 2244.

Said material is known to have a maximum torque (MH) of 43±7 dN.m and a minimum torque (ML) of 16±4.5 dN.m.

The maximum torque is generally correlated with durometer hardness and/or modulus.

Moreover in comparison to silicone, which is a material classically used for sealing medical devices, butyl-type rubber has the advantage of being less permeable to moisture and air and presenting better barrier properties.

For example, the bromobutyl rubber is a material of choice as it gives low absorption of preservatives and antimicrobial components contained in insulin on its surface.

As mentioned above, the at least one O-ring 4 or 4' is maintained on the stopper 2 by a correct positioning in the at least one respective peripheral groove 210 or 210'.

The shape and dimension of these peripheral grooves 210 or 210' are important parameters as they influence the behavior of the O-ring 4 or 4' when the stopper 2 is gliding along the walls of the container body 1.

Figure 4A:
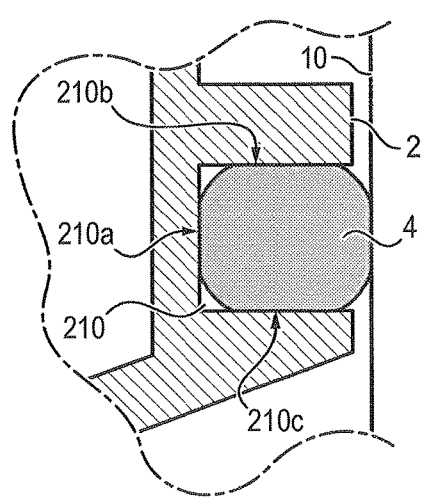
FIGS. 4A and 4B are schematic comparative sectional views of the seal within the groove of a stopper according to an embodiment of the invention and of a stopper of a known injection device, respectively.

As shown on FIG. 4A, the peripheral groove 210 or 210' has preferably a U-shaped cross-section, i.e. a side wall 210*a* that extends axially (i.e. parallel to the axis X and to the inner wall 10 of the container body 1), and two parallel lateral walls 210*b*, 210*c* that extend radially (i.e. perpendicularly to the side wall 210*a*) from the side wall 210*a* towards the inner wall 10 of the container body 1.

The U-shaped peripheral groove cooperates with the wall of the container body 1 to form a sealed housing having a substantially rectangular cross-section defined by the walls 210*a*, 210*b*, 210*c* and the inner wall 10 of the container body 1.

This O-ring housing is shown as a hatched rectangle on the left on FIG. 5(*a*).

Since the sealing with respect to the container body 1 is not ensured by the stopper 2 itself, there is not a tight fit between the stopper 2 and the container body 1, i.e. the lateral walls 210*b*, 210*c* are not in contact with the wall of the container body 1.

The interval between the stopper 2 and the container body 1 is locally filled in by the O-ring 4 or 4'.

Figure 4B:
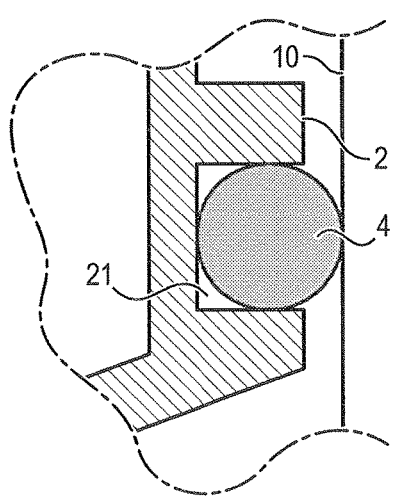

In existing medical injection devices, the O-ring 4 is maintained in a peripheral groove having a cross-section that substantially circumscribes the circular cross-section of the O-ring 4 (see FIG. 4B).

This kind of peripheral groove is not appropriate as it does not exert a significant compression on the O-ring 4, whereas in the medical injection device according to the invention, the rectangular cross-section of the O-ring housing provides both a radial and an axial compression of the O-ring 4.

In other words, the three walls of the peripheral groove 210 of the stopper 2 and the inner wall 10 of the container body 1 exert a compressive force onto the O-ring 4, which results in a flattening of the O-ring 4 on these four interfaces, as shown on FIG. 4A.

The O-ring 4 is thus better maintained in the peripheral groove 210 of the stopper 2.

Moreover, the cross-section of said peripheral groove 210, 210' is defined by a certain width (noted w) and a certain height (noted h) (see FIG. 5(a)).

It is to be noted that due to the circular shape of the O-ring 4, the O-ring 4 is mainly in contact with a central part of the walls defining the peripheral groove 210, 210'.

In particular, the corners of the rectangle delimiting the cross-section of the peripheral groove 210, 210' correspond in fact to dead zones that are not intended to be in contact with the O-ring 4.

Hence, although the peripheral groove 210, 210' has been represented in the appended drawings with a cross-section having a rectangular form, the peripheral groove may have rounded corners between the axial side wall 210a and each of the lateral walls 210b, 210c without departing from the scope of the invention.

In this respect, the width w has to be understood as being the distance between the parts of the lateral walls 210b, 210c that are in contact with the O-ring 4 and the height h means the distance between the part of the axial wall 210a that is in contact with the O-ring and the outer surface of the stopper 2.

Considering the width w, it has to be chosen very smartly in order to control the behavior of the O-ring 4, that is to say, on the one hand, to avoid any play of the O-ring 4 into the peripheral groove 210 and, on the other hand, to avoid a compression that would be inappropriately high.

Indeed, said width w has an influence on the axial compression of the O-ring 4 and therefore needs to be under control in order not to disturb its global compression which is mainly driven by the radial compression.

In addition, the dimensioning of the height h of the cross-section of said peripheral groove 210, 210' is also of importance because, in combination with the width w, it is an essential parameter of the good positioning of the O-ring 4 into the peripheral groove 210, 210' either when the stopper 2 is in movement within the container body 1 or when it is at rest.

An uncontrolled height h would indeed lead to a bad compression profile of the O-ring 4; for example, if the height h is too small as compared to the diameter of the O-ring, said O-ring 4 would tend to be jammed into the gap formed by the left space between the inner wall 10 of the container body 1 and the outer surface of the stopper 2.

Besides, the cross-section of said peripheral groove 210, 210' is also defined by an outer groove diameter g of the stopper 2 (see FIG. 5(a)) that allows controlling the compression of the O-ring 4 and therefore controlling the tightness of the stopper 2.

Indeed, a good dimensioning of said outer groove diameter g of the stopper 2 enables a right tightening of the O-ring 4.

In the case said outer groove diameter g would be too high, it would contact the inner wall 10 of the container body 1, leading to a bad functioning of the stopper 2 within the container body 1 with potential gliding problems.

Generally speaking, the good functioning of said stopper 2 results from the combination of the dimensions of the cross section of the peripheral groove 210, 210' of the stopper 2 as detailed above as well as of the material characteristics of the O-ring 4.

Otherwise said, the global compression of the O-ring 4 is significantly impacted by the material characteristics of the butyl-type rubber O-ring 4, which properties allow obtaining a good deformation combined to a high stability of the O-ring 4 into the cross section of the peripheral groove 210, 210'. As a consequence, since there is a right fit between the O-ring 4 and the peripheral groove 210, the inaccuracy of the dose delivery is significantly reduced.

The dimensioning of the diameter of the O-ring 4 and the dimensioning of the cross-section of the peripheral groove of the stopper 2 depend on the material of the O-ring 4, in particular on its hardness.

For example, if the diameter of the O-ring at rest is of 1.60 mm, the corresponding peripheral groove has a U-shaped cross-section defined by a width w smaller than or equal to 1.85 mm, preferably comprised between 1.60 mm and 1.80 mm, and a height h greater than or equal to 0.86 mm, preferably greater than or equal to 0.95 mm.

In the case where the O-rings 4, 4' have circular cross-sections with different diameters, it is preferred to have the distal O-ring with a larger diameter and the proximal O-ring with a smaller diameter.

As mentioned above, butyl-type rubber is a generally preferred material for the O-ring 4 as it is harder than silicone.

Figure 1:
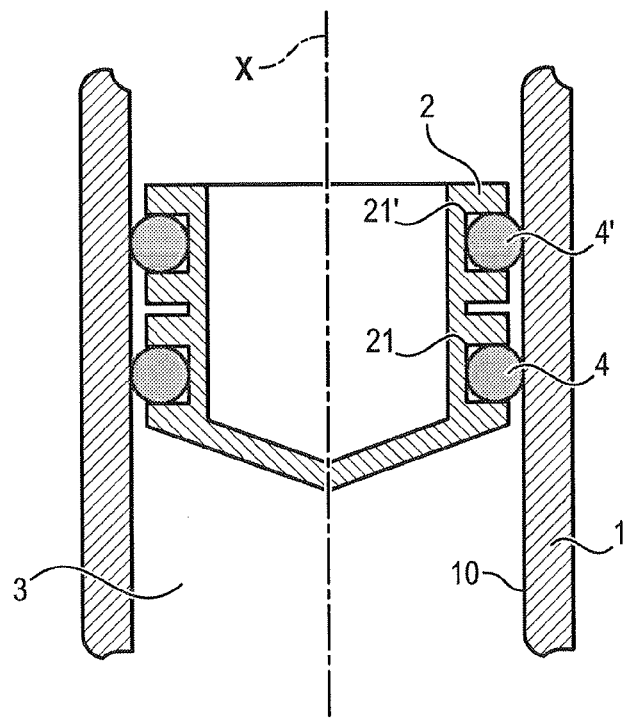
FIG. 1 is a schematic sectional view of the gliding engagement of a stopper of the prior art into a container body.

The Table 1 below shows the comparison between the axial and radial compression obtained with a known injection device (as illustrated on FIGS. 1, 4B and 5(b)) and with a device according to an embodiment of the present invention (illustrated on FIGS. 2, 4A and 5(a)).

TABLE 1

|  | Known device with 2 silicone O-rings and siliconized stopper | Device according to an embodiment of the invention with a rigid stopper and 2 siliconized butyl-type rubber O-rings |
|---|---|---|
| Axial compression | 0% | 14.4% |
| Radial compression | 6.25% | 20% |

With reference to FIGS. 5(a) and 5(b), the radial compression is defined as being the ratio between:
- the difference between the diameter Ø of the O-ring 4 in a rest state and the distance d between the inner wall 10 of the container body 1 and the sidewall 210a of the peripheral groove 210 of the stopper 2 (said distance d being referred to as the depth of the O-ring housing), and
- the diameter Ø of the O-ring 4 in a rest state.

The axial compression is defined as being the ratio between:
- the difference between the height (i.e. the dimension in the axial direction X) of the O-ring 4 which has become elliptic due to the above-calculated radial compression, and the width (w) of the peripheral groove 210, i.e. the distance between lateral walls 210b and 210c, and
- the height of the elliptic O-ring 4.

It appears that in the case of the known device, the peripheral groove 21 of the stopper 2 does not exert any axial compressive force onto the O-ring 4.

As a consequence, when the gliding of the stopper 2 is initiated, the force exerted by the plunger rod is first used to move the stopper 2 with respect to the O-ring 4, and as a second step only, the O-ring 4 moves up with the stopper 2.

Hence, the delivered dose is smaller than the intended dose with the known device.

To the contrary, with the device according to the present invention, the O-ring 4 is significantly compressed both radially and axially thanks to the correct shape of the peripheral groove 210.

Therefore, when the gliding of the stopper 2 is initiated, the force exerted by the plunger rod is immediately used to displace both the stopper 2 and each O-ring 4, 4' at the same time.

Moreover, since the O-ring is in a hard material such as butyl-type rubber, the O-ring is less subject to deformation induced by the force applied with the plunger rod and thus it remains more stable than an O-ring in silicone.

A further effect of this optimized compression of the O-ring within the peripheral groove is that the O-ring is not likely to twist upon actuation of the stopper.

The Table 2 below illustrates the accuracy rate of delivery obtained with a known device (as illustrated on FIGS. 1 and 5(b)) and with a device according to an embodiment of the present invention (illustrated on FIGS. 2 and 5(a)).

The accuracy rate is defined as the difference between the theoretical dose that should have been delivered and the measured dose actually delivered.

The accuracy rate is given for different conditions of delivery namely:
- unit(s) of dose that corresponds to the delivered concentration unit of insulin that is measured in mg/ml, knowing that 1 unit=3.4 mg/ml, such data corresponding to the bolus of insulin delivered, i.e. a sporadic, instantaneous delivery, or
- units of dose per hour, such data corresponding to a basal delivery, meaning a continuous delivery of insulin delivered all day long.

The reactivity is the time spent by the stopper to reach the linearity in the drug delivery, meaning a continuous and homogeneous delivery flow rate.

The reactivity of the stopper has been studied by comparing the results between a known device with two silicone O-rings and a siliconized stopper and, a device according to an embodiment of the invention having two siliconized O-rings and a stopper.

As shown below, a device according to the invention has an improved stopper reactivity than known devices, meaning that the accuracy of the delivered dose is more accurate.

TABLE 2

| Delivery accuracy rate (% of error) | Known device | Device according to an embodiment of the invention |
|---|---|---|
| 1 unit of dose | −2.4% | −0.5% |
| 10 units of dose | −2% | 1% |
| 2 units of dose/hour | −1.1% | −0.9% |
| Reactivity of the stopper (seconds) | 124 s | 12 s |

In another embodiment, the O-rings and/or at least part of the inner wall of the container body can be coated with a lubricant layer such as a silicone layer.

In yet another embodiment, the inner wall of the container body and/or the O-rings are lubricated before being submitted to a cross-linking done for example by irradiation, the irradiation providing a gel structure to the lubricant layer.

For example such kind of lubricant can comprise a mixture of non-reactive silicone and reactive silicone:
"reactive silicone" meaning a silicone polymer comprising at least one reactive functional group, i.e. a functional group that polymerizes under usual conditions of irradiation (e.g. Gamma or UV irradiation). A reactive functional group usually comprises at least one chemical bond that is able to break under irradiation and link up with another functional group for creating a polymer, "non-reactive" silicone meaning a silicone polymer that only comprises non-reactive functional groups, i.e. functional groups that do not polymerize under usual conditions of irradiation, and that does not comprise any reactive functional group as defined above. For example, linear alkyl chains are considered to be non-reactive functional groups within the meaning of the present invention.

On the one hand, the non-reactive silicone consists advantageously in poly-(dimethylsiloxane) with a viscosity of 12500 cSt at 25° C. and its amount is comprised between 80 and 90% by weight of the total weight of the lubricant composition.

On the other hand, the reactive silicone comprises advantageously a mixture of vinyl-based silicone and acrylate-based silicone, the amount of vinyl-based silicone being comprised between 8 and 15% by weight, and the amount of the acrylate-based silicone being comprised between 2 and 5% by weight.

More preferably, the amount of vinyl-based silicone in the lubricant composition is of 10% by weight, whereas the amount of the acrylate-based silicone in the lubricant composition is of 3% by weight.

In a preferred lubricant composition, the vinyl-based silicone comprises a trimethylsilyl terminated vinylmethylsiloxane-dimethylsiloxane copolymer and the acrylate-based silicone comprises a trimethylsilyl terminated acryloxypropylmethylsiloxane-dimethylsiloxane copolymer.

The above-mentioned irradiation has the effect of cross-linking the lubricant layer which becomes a gel having the following characteristics:
- a gel fraction comprised between 25 and 55% by weight,
- a shear viscosity comprised between 500 and 2000 Pa.s for a shear rate of 0.1 rad/s at 25° C., and
- a phase angle comprised between 20° and 40° for a shear rate of 0.1 rad/s at 25° C.

Preferably, said irradiation is Gamma irradiation, e.g. carried out by a Cobalt-60 source.

Due to its gel structure, the lubricant layer provides a very low rate of particles released into the pharmaceutical solution.

In this way, when the irradiated lubricant layer is a silicone layer or a mixture containing silicone, the release of silicone droplets into the solution is minimized or even avoided.

The irradiation treatment of the lubricant layer can be required as it has been shown that a layer with a gel structure improves the gliding properties of the stopper, but also that the stability of the O-rings regarding sterilization treatments is increased.

It has also been demonstrated that this treatment enhances the stability of these O-rings over time (including during a storage time between 12 to 24 months).

FIG. 6 illustrates an example of an injection pump 5 for delivering a fluid to a patient, the fluid being contained in the container body 1 of an injection device according to embodiments of the present invention.

The injection device is filled with the fluid to be administered to the patient.

The injection device is preferably a prefilled container ready to be used or can be a container to be filled manually from a vial before to be plugged within the pump 5.

The architecture of the pump 5 is known per se and therefore will not be described here in detail.

The pump 5 comprises a housing 50 for receiving an injection device as described above.

The loading of the injection device inside the housing 50 of the pump is performed via the proximal part of the stopper 20 that is connected to a plunger rod 51.

The plunger rod 51 is driven by a motor 52 toward the distal opening of the injection device, so as to expel a given dose of the fluid through said opening.

The housing advantageously comprises a display 54 and a plurality of buttons 53 for controlling the pump 5.

The invention has been described above with reference to embodiments given by way of an example. Of course, it is not limited to these embodiments and extends to all other embodiments covered by the appended claims.

The invention claimed is:

1. A medical injection device, comprising:
a container body having an inner wall, and a stopper in gliding engagement with the inner wall of the container body for expelling a fluid through an opening of said container body,
wherein at least a distal portion of the stopper is made of a thermoplastic polyolefin,
wherein the stopper defines at least one peripheral groove and the medical injection device further comprises at least one O-ring made of a butyl-type rubber maintained in the at least one peripheral groove,
and wherein the at least one peripheral groove has a U-shaped cross-section comprising a sidewall extending axially a width w and two parallel lateral walls extending radially from the sidewall a height h, wherein the height h of the at least one peripheral groove is less than the width w of the at least one peripheral groove, and
the cross-section of said at least one peripheral groove of the stopper compresses the at least one O-ring in an axial direction and a radial direction when said at least one O-ring is engaged in the peripheral groove between the stopper and the inner wall of the container body providing a progressive contact of the O-ring with the inner wall of the container body.

2. The device of claim 1, wherein the compression of said at least one O-ring in the axial direction is at least 14.4% and the compression of the at least one O-ring in the radial direction is at least 20%.

3. The device of claim 1, wherein the diameter of said at least one O-ring at rest is greater than the width w of the at least one peripheral groove.

4. The device of claim 1, wherein the material of said at least one O-ring is bromobutyl.

5. The device of claim 1, wherein the stopper further defines a second peripheral groove and the device further comprises a second O-ring maintained in the second peripheral groove.

6. The device of claim 5, wherein the distance between said O-ring and said second O-ring is at least equal to the diameter of the stopper.

7. The device of claim 5, wherein said O-ring and said second O-ring each have a circular cross-section the diameters of the O-ring being different than the diameter of the second O-ring.

8. The device of claim 7, wherein the diameter of the O-ring at a distal location is larger than the diameter of the O-ring at a proximal location.

9. The device of claim 1, wherein said at least one peripheral groove forms with the container body an O-ring housing having a rectangular cross-section.

10. The device of claim 9, wherein the diameter of said at least one O-ring is 1.60 mm and said at least one peripheral groove has a U-shaped cross-section defined by the width w smaller than or equal to 1.85 mm and the height h greater than or equal to 0.86 mm.

11. The device of claim 10, wherein said at least one peripheral groove has a U-shaped cross-section defined by the width w of between 1.60 mm and 1.80 mm and the height h greater than or equal to 0.95 mm.

12. The device of claim 9, wherein a depth of said O-ring housing is smaller than the width thereof.

13. The device of claim 1, wherein the container body comprises a fluid therein.

14. The device of claim 13, wherein the fluid is insulin.

15. The device of claim 1, wherein at least one of said at least one O-ring and at least part of the inner wall of the container body is coated with a lubricant layer.

16. The device of claim 15, wherein said lubricant layer is a gel comprising a mixture of acrylate-based silicone, vinyl-based silicone and polydimethylsiloxane.

17. A pump for delivering a fluid to a patient, comprising:
a housing for receiving an injection device containing said fluid, said injection device comprising a container body having an inner wall and a stopper in gliding engagement with the inner wall of the container body for expelling a fluid through an opening of said container body,
wherein at least a distal portion of the stopper is made of a thermoplastic polyolefin,
wherein the stopper defines at least one peripheral groove and the injection device further comprises at least one O-ring made of a butyl-type rubber maintained in the at least one peripheral groove, and
wherein the cross-section of said at least one peripheral groove of the stopper compresses the at least one O-ring in an axial direction and a radial direction when said at least one O-ring is engaged in the peripheral groove between the stopper and the inner wall of the container body, wherein the at least one peripheral groove has a U-shaped cross-section comprising a sidewall extending axially a width w and two parallel lateral walls extending radially from the sidewall a height h, wherein the height h of the at least one peripheral groove is less than the width w of the at least one peripheral groove wherein the at least one O-ring within the at least one peripheral groove provides a progressive contact of the O-ring with the inner wall of the container body,
a plunger rod arranged in said housing and connected to a proximal part of the stopper of said injection device, and
a motor for driving said plunger rod so as to expel the fluid from the opening of the injection device.

18. The device of claim 1, wherein the compression of the at least one O-ring in the radial direction is greater than the compression of the at least one O-ring in the axial direction.

19. The pump of claim 17, wherein the compression of the at least one O-ring in the radial direction is greater than the compression of the at least one O-ring in the axial direction.

20. A medical injection device, comprising:
a container body having an inner wall, and a stopper in gliding engagement with the inner wall of the container body for expelling a fluid through an opening of said container body,
wherein at least a distal portion of the stopper is made of a thermoplastic polyolefin,
wherein the stopper defines at least one peripheral groove and the medical injection device further comprises at least one O-ring made of a butyl-type rubber maintained in the at least one peripheral groove, wherein the cross-section of said at least one peripheral groove of the stopper compresses the at least one O-ring in an axial direction and a radial direction when said at least one O-ring is engaged in the peripheral groove between the stopper and the inner wall of the container body, wherein the at least one peripheral groove has a U-shaped cross-section comprising a sidewall extending axially and two parallel lateral walls extending radially from the sidewall, and wherein the O-ring interfaces with the sidewall, the two parallel lateral walls, and the inner wall of the container body and is flattened on each of the interfaces with the sidewall, the two parallel lateral walls, and the inner wall of the container body providing a progressive contact of the O-ring with the inner wall of the container body.

21. The device of claim 1, wherein the at least one O-ring is flattened on four interfaces comprising the sidewall and the two parallel lateral walls of the at least one groove and the inner wall of the container body and wherein end portions of the parallel lateral walls adjacent the inner wall of the container body are out of contact with the inner wall of the container body and the engagement of the stopper with the inner wall of the container body is achieved solely via the O-ring.

22. The pump of claim 17, wherein the at least one O-ring is flattened on four interfaces comprising the sidewall and the two parallel lateral walls of the at least one groove and the inner wall of the container body, and wherein end portions of the parallel lateral walls adjacent the inner wall of the container body are out of contact with the inner wall of the container body and the engagement of the stopper with the inner wall of the container body is achieved solely via the O-ring.

23. The device of claim 20, wherein the at least one O-ring is flattened on four interfaces comprising the sidewall and the two parallel lateral walls of the at least one groove and the inner wall of the container body, and wherein end portions of the parallel lateral walls adjacent the inner wall of the container body are out of contact with the inner wall of the container body and the engagement of the stopper with the inner wall of the container body is achieved solely via the O-ring.

24. The device of claim 1, wherein the sidewall and two parallel lateral walls of the at least one groove cooperate to form corners within the at least one groove so that upon flattening of the at least one O-ring, dead zones are created in the corners.

25. The pump of claim 17, wherein the sidewall and two parallel lateral walls of the at least one groove cooperate to form corners within the at least one groove so that upon flattening of the at least one O-ring, dead zones are created in the corners.

26. The device of claim 20, wherein the sidewall and two parallel lateral walls of the at least one groove cooperate to form corners within the at least one groove so that upon flattening of the at least one O-ring, dead zones are created in the corners.

* * * * *